United States Patent [19]

La Gro

[11] Patent Number: 5,468,235
[45] Date of Patent: Nov. 21, 1995

[54] OSTOMY POUCH AND FILTER ASSEMBLY WITH SUCCESSIVE FLAP VENTS

[75] Inventor: Phillip A. La Gro, Hawthorn Woods, Ill.

[73] Assignee: Hollister Incorporated, Libertyville, Ill.

[21] Appl. No.: 398,768

[22] Filed: Mar. 6, 1995

[51] Int. Cl.$^6$ ........................................... A61F 5/44
[52] U.S. Cl. ............................................... 604/333
[58] Field of Search .................................. 604/327, 328, 604/332, 333, 334, 335, 338, 344, 355, 356, 277

[56] References Cited

U.S. PATENT DOCUMENTS

| | | | |
|---|---|---|---|
| 4,203,445 | 5/1980 | Jessup et al. | 604/333 |
| 4,274,848 | 6/1981 | La Gro | 604/333 |
| 5,306,264 | 4/1994 | Ferguson et al. | 604/332 |

Primary Examiner—Randall L. Green
Assistant Examiner—Dennis Ruhl
Attorney, Agent, or Firm—Tilton Fallon Lungmus

[57] ABSTRACT

An ostomy pouch is disclosed having a filter assembly located therein, the filter assembly including a thin, flexible outer panel of liquid- and gas-impervious sheet material having a peripheral portion sealed to one wall of the pouch and a central portion unattached to, and preferably spaced from, that wall. The pouch wall overlying the central portion of the filter assembly's outer panel is provided with a flap vent in the form of a curvilinear slit defining at least one flap that normally assumes a closed position coplanar with surrounding portions of the wall but flexes outwardly into open position when venting gases from the pouch. The outer panel of the filter assembly is provided with a second flap vent similar to, but preferably out of register with, the first flap vent of the pouch wall, and components of the filter assembly within the pouch function to brace the flap (or flaps) of the second vent against opening in any direction other than outwardly.

10 Claims, 1 Drawing Sheet

U.S. Patent  Nov. 21, 1995  5,468,235
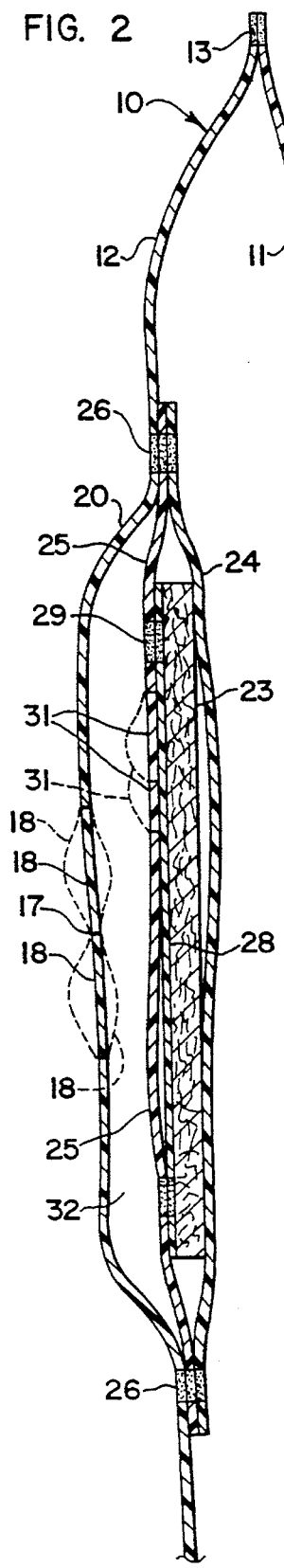
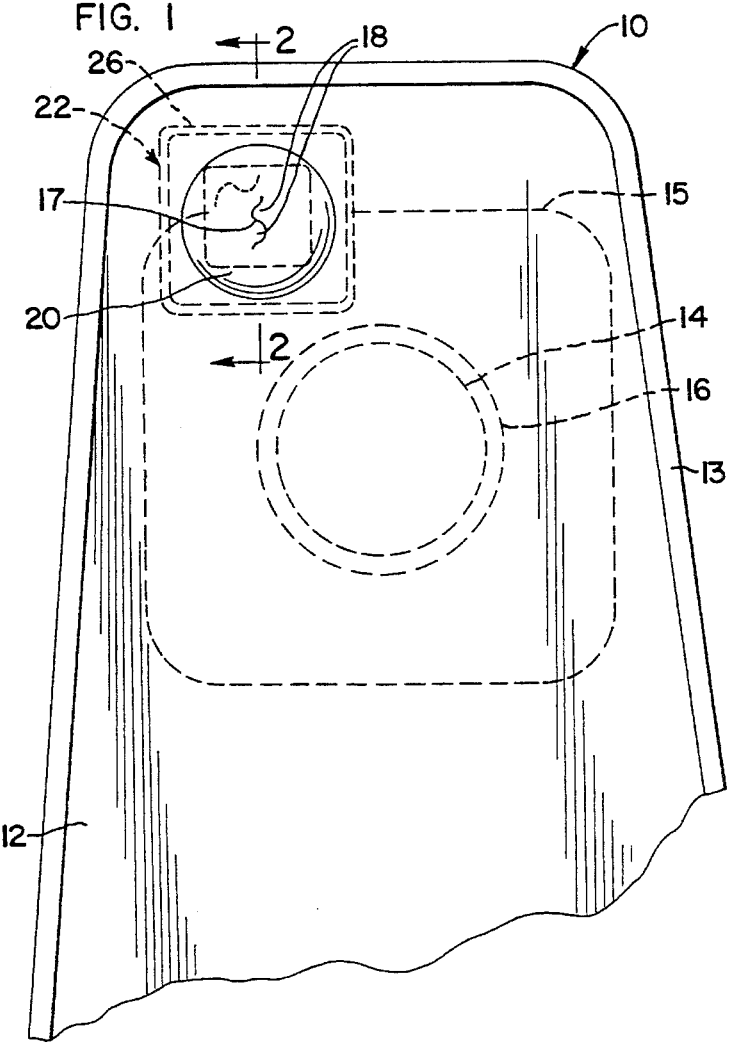
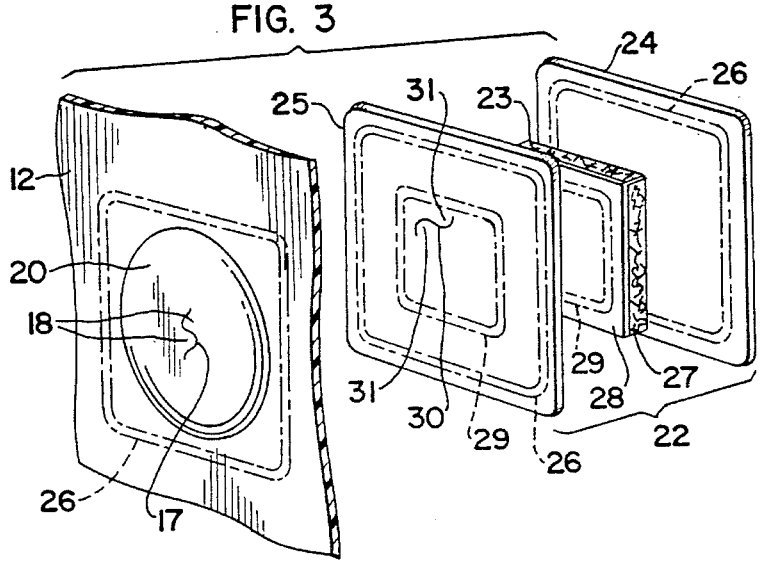

OSTOMY POUCH AND FILTER ASSEMBLY WITH SUCCESSIVE FLAP VENTS

BACKGROUND OF THE INVENTION

U.S. Pat. Nos. 4,203,445 and 4,274,848 disclose ostomy pouches in which deodorizing gas filters are mounted. The wall portions of the pouches that overlie the filters are dome-shaped and provided with S-shaped slits for venting gases from the pouches. The slits serve as normally-closed flap valves with the flaps flexing outwardly into open positions when gas pressure within the pouches exceeds ambient pressure.

While the S-shaped flap vent of such a pouch assumes a closed condition in the absence of a pressure differential or other force, it is possible that the flap (or flaps) might also flex inwardly to allow liquid to enter a pouch when, for example, such a pouch is worn by an ostomate while taking a shower. Although only a small amount of water would be expected to pass inwardly through such vent opening, the volume necessary to cause an adverse effect on filter operation would also be small.

The present invention addresses this concern by providing a construction in which a filter assembly is provided with a second flap vent behind, but preferably out of register with, the flap vent of the pouch. More specifically, the filter assembly comprises a planar deodorizing gas filter enclosed in a flat envelope composed of an inner panel of gas-permeable but liquid-impervious sheet material and an outer panel of gas- and liquid-impervious sheet material. The outer panel has its peripheral portion sealed to the wall of the pouch along a continuous seal line spaced from and extending about the flap vent of the pouch. A flat vent chamber is thereby formed (or develops in use) between the pouch wall and the central portion of the filter assembly's outer panel. It is the panel's central portion that is provided with a second flap vent in the form of a curvilinear slit defining at least one flap that normally assumes a closed position coplanar with the panel's central portion but that is capable of flexing outwardly into an open position to vent gases from the pouch when the pressure therein exceeds ambient pressure. Filtered gases entering the vent chamber may then pass outwardly from that chamber through the flap vent in the pouch wall.

The second flap vent—the one provided by the filter assembly—also performs a security function in protecting the filter against liquid contact. Thus, in the shower, a small amount of water might enter the vent chamber should a spray of water impinge on the flap or flaps of the pouch vent, since such flaps are free to flex inwardly as well as outwardly. In contrast, the flap or flaps of the vent in the central portion of the filter assembly's outer panel tend to remain closed, partly because they are shielded by the pouch wall against direct contact by such a spray and partly because they are braced by the planar gas filter disposed directly therebehind. Unlike the flaps of the pouch vent, the flaps of the filter vent, although free to flex outwardly into open positions in the vent chamber in response to increasing gas pressure within the pouch, are restrained against inward flexure by the remainder of the filter assembly located within the pouch. Because of the relationship of parts, the flap vent of the filter assembly essentially functions as a one-way valve, in contrast to the flap vent of the pouch wall which allows flow in either direction.

The flap vents of the pouch and filter assembly preferably assume the configuration of S-shaped slits, each slit thereby defining two flaps. While the flap vents are necessarily in close proximity because of the relatively small size of the filter assembly, it is desirable that they not be in register with each other. Most advantageously, two flap vents are not only out of register but are laterally displaced so that the flaps of one vent cannot interfere with or directly affect the operation of the flaps of the other vent.

Other features, advantages, and objects will become apparent from the specification and drawings.

DRAWINGS

FIG. 1 is a fragmentary plan view of an ostomy pouch equipped with a filter assembly and provided with tandem flap vents, one formed in the pouch wall and the other provided by an internal filter assembly.

FIG. 2 is an enlarged vertical sectional view taken along line 2—2 of FIG. 1.

FIG. 3 is an exploded perspective view showing a portion of the pouch wall and the filter assembly therebehind.

DETAILED DESCRIPTION OF PREFERRED EMBODIMENTS

Referring to the drawings, the numeral 10 generally designates an ostomy pouch having first and second walls 11 and 12 formed of flexible fluid-impermeable thermoplastic sheet material. The walls are joined around their peripheries by heat-sealing 13 or by any other suitable connecting means. Any effective gas- and liquid-impervious thermoplastic material may be used for fabrication of the walls such as, for example, a polyolefin film laminated with an appropriate barrier material. A particularly suitable commercial material comprises low-density polyethylene coextruded with a coextensive layer or core of polyvinylidene chloride, such material being commercially available under the Trademark "SARANEX" from Dow Chemical Company, Midland, Mich.

Wall 11, in accordance with standard pouch construction, is provided with a stoma-receiving opening 14 shown in dotted lines in FIG. 1. The outline of an adhesive attachment patch 15 is also illustrated. The patch is secured by heat sealing at 16 to the outside of wall 11 around the opening 14. The rear surface of the patch may be coated with a pressure-sensitive medical adhesive so that after removal of a protective backing sheet from the adhesive, the ostomy appliance may be adhered directly to the skin about a stoma.

It is to be understood while the filtering and venting features of this invention are to be described in detail in connection with a one-piece appliance, they may also be utilized with what is commonly referred to as a two-piece appliance. In the latter case, the adhesive patch 15 would be replaced by a coupling ring adapted to be mechanically or adhesively joined to a faceplate which in turn would be capable of adhesive attachment to the skin surfaces about a patient's stoma. Since both one-piece and two-piece appliances are well known in the art, and since the form of attachment of an appliance to a patient constitutes no part of this invention, further description of such attachment means is believed unnecessary herein.

One wall of the pouch, preferably the second or front wall 12, is provided with a vent 17 located near the upper end of the pouch. The vent takes the form of a curvilinear slit defining at least one flap that normally assumes a closed position generally coplanar with the immediately surrounding portions of the wall but is capable of flexing outwardly into an open position to vent gases from the pouch when the pressure therein exceeds ambient pressure. In the embodiment illustrated, the slit is S-shaped and defines a pair of arcuate flaps 18 facing in opposite directions. If desired, the curvilinear slit may be extended even further to define one or more additional flaps, all of which would function as flexible closure elements that tend to be self-closing in the absence of a pressure differential.

Slit 17 preferably extends generally vertically and is located in a bubble-like protrusion 20 formed in the flexible wall 12 of the pouch. The structure and functions of the bubble configuration, as well as of the slit and its closure flaps, are discussed in detail in the aforementioned co-owned U.S. Pat. Nos. 4,203,445 and 4,274,848, the disclosures of which are incorporated by reference herein.

A deodorizing filter assembly 22 is secured to walls 12 within pouch 10 adjacent vent 18. The filter assembly 22 includes a planar filter element 23 in an envelope composed of a pair of thermoplastic panels 24 and 25. The two panels are larger in outline than the filter and have their peripheral edges joined together along a continuous heat seal line 26. In addition, the envelope is joined to wall 12 of the pouch either by the same heat seal 26 (as shown) or by an adjacent seal line that extends continuously about the periphery of the envelope and about vent 17, all at a substantial distance outwardly from that vent. (In the exploded perspective view of FIG. 3, the location of the seal line 26 on each of the panels 24 and 25 and on the wall 12 of the pouch is indicated in phantom.)

In the illustration given, the filter assembly 22 and its components are shown as being substantially square in outline, but it is to be understood that other configurations, such as circular, may be used.

The planar filter element 23 is composed of at least two layers: a relatively thick fibrous filter layer 27 formed of or impregnated by activated carbon and a relatively thin cover layer 28 composed of a heat-sealable, gas-permeable, liquid-repellent sheet material such as, for example, a non-woven polyester cellulose fabric sheet material saturated with fluorocarbons and marketed under the designation 088-8852 by Precision Fabrics, Greensboro, N.C. Other non-woven fabrics that are gas-permeable, heat-sealable, and resistant to the passage of water therethrough may be used, such as a reinforced non-woven cellulosic material sold under the Trademark "KAYCEL" by Kimberly-Clark Corporation, Neenah, Wis.; a porous, expanded, high-density polyethylene or polypropylene film of the type marketed under the designation "Delnet" by Hercules Incorporated, Wilmington, Del.; or a microporous polytetrafluoroethylene marketed under the Trademark "GORTEX" by W. L. Gore & Associates, Newark, Del.

The cover layer 28 is heat sealed to the outer panel 25 of envelope 22 along a continuous heat seal line 29 that extends along the periphery of cover layer 28 inboard of the heat seal line 26 that joins together the panels of the envelope and secures that envelope to wall 12 of the pouch.

The inner panel 24 may be formed of the same heat-sealable gas-permeable, liquid-repellent (or resistant) sheet material used for cover layer 28. Outer panel 25 of the envelope may be formed of any flexible, heat-sealable sheet material that is gas- and liquid-impermeable. Low density polyethylene has been found particularly effective, but other materials having similar properties may be used.

Like wall 12 of the pouch, panel 25 of the filter assembly 22 is provided with a flap vent in the form of a curvilinear slit 30 defining at least one flap 31 that normally assumes a closed position coplanar with panel 25 but capable of flexing outwardly into an open position to vent gases from pouch 10. An S-shaped slit 30 that results in a pair of arcuate flaps 31 facing in opposite directions is believed particularly effective. If desired, the curvilinear slit 30 may be extended in length to provide additional flaps or, alternatively, may be reduced to provide only a single arcuate flap.

It will be observed from FIG. 3 that the flap vent 30 of the filter assembly 22 is offset with respect to the center of outer panel 25. More specifically, vent slit 30 is located within the central portion of the panel delineated by the inner heat seal line 29 but is not centered within that portion and does not register with slit 17. With panels 24 and 25 of the filter assembly heat sealed to pouch wall 12 along a line 26 located as depicted in FIG. 3, or at 90, 180, or 270 degree rotations of the assembly from that position, flap vent 30 will always be offset with respect to flap vent 17.

Of particular importance is the fact that outer panel 25 is heat sealed to layer 28 of filter 23 with its central portion extending over the thermoplastic front layer 28 of the planar filter, preferably in direct contact with that layer. As indicated by broken lines in FIG. 2, the flaps 18 of vent 17 are capable of flexing both outwardly and inwardly depending on the direction of applied force or pressure. However, while the flaps 31 of vent 30 are free to flex outwardly (the only attachment between filter 23 and panel 25 being heat seal line 29), inward flexing of the flaps is blocked or at least restrained by the relatively stiff, planar filter 23 directly therebehind. The flaps of vent slit 30 therefore coact with filter 23 to perform a one-way valving function. Gases passing through the filter may readily exit through flap 30 into the space or chamber 32 defined by bubble 20, with such gases then exiting to atmosphere through flap vent 17 of the pouch. However, should liquid (or any other foreign matter) enter space 32, it cannot readily contact filter 23 because the flaps 31 of vent 30 are restrained from flexing inwardly.

While it is preferred that pouch wall 12 be formed with an outwardly protruding bubble or dome 20, it should be understood that the advantages of this invention may be achieved, although possibly to a lesser extent, even if bubble 20 were eliminated and vent slit 17 were formed in a flatter portion of wall 12. The bubble insures that the flaps 31 of the inner vent of the filter assembly are free to flex outwardly into open positions, without any restraint imposed by the pouch wall, as pressure within the bag increases. However, even in the absence of a pre-formed bubble 20, a space or vent chamber 32 will tend to develop in use because of the flexibility of the pouch wall and the fact that it is secured to the filter assembly 22 along a line 26 located a substantial distance outwardly from vent 17, and because outwardly-flowing gases could be expected to inflate the space and cause that portion of the pouch wall within the limits of heat seal 26 to bow or bulge slightly outwardly.

While in the foregoing, I have disclosed an embodiment of the invention in considerable detail for purposes of illustration, it will be understood by those skilled in the art that many of these details may be varied without departing from the spirit and scope of the invention.

I claim:

1. An ostomy pouch having first and second walls of flexible polymeric film sealed to each other about their edges; one of said walls having a first flap vent in the form of a curvilinear slit defining at least one flap normally assuming a closed position coplanar with immediately surrounding portions of said one wall but flexing outwardly into an open position to vent gases from said pouch when the pressure therein exceeds ambient pressure; and a deodorizing filter assembly secured to said one wall within said pouch for deodorizing gases exiting said pouch through said first flap vent; said assembly including a planar filter enclosed in a flat envelope having an inner panel of gas-permeable liquid-impervious sheet material and an outer panel of flexible gas- and liquid-impervious sheet material; said outer panel being sealed to said one wall of said pouch along a continuous seal line spaced from and extending about said first flap vent to define a vent chamber between said outer panel and said one wall; wherein the improvement comprises said outer panel of said filter assembly being provided with a second flap vent in the form of a curvilinear slit defining at least one flap normally assuming a closed position coplanar with said outer panel but capable of flexing outwardly into said vent chamber to vent gases from said pouch; said flap of said second flap vent being restrained against inward flexure by contact with said planar filter of said assembly.

2. The ostomy pouch of claim 1 in which each of said flap vents has the configuration of an S-shaped slit.

3. The ostomy pouch of claim 1 in which said one wall of said pouch has a dome-shaped portion aligned with said filter assembly, thereby spacing said one wall from said outer panel to form said vent chamber.

4. The ostomy pouch of claim 1 in which said planar filter includes a layer of porous odor-absorbing filter material and a cover layer of gas-permeable but water-repellent sheet material; said cover layer being disposed directly behind and immediately adjacent said outer panel of said filter assembly.

5. The ostomy pouch of claim 4 in which said cover layer and said outer panel are each formed of thermoplastic material and are heat sealed to each other along a second continuous seal line spaced from and extending about said second flap vent and inboard of said continuous seal line joining said outer panel to said one wall of said pouch.

6. An ostomy pouch having first and second walls of flexible polymeric film sealed to each other about their edges; one of said walls having a first flap vent in the form of a curvilinear slit defining at least one flap normally assuming a closed position coplanar with immediately surrounding portions of said one wall but flexing outwardly into an open position to vent gases from said pouch when the pressure therein exceeds ambient pressure; and a deodorizing filter assembly secured to said one wall within said pouch for deodorizing gases exiting said pouch through said first flap vent; said assembly including a planar filter enclosed in a flat envelope having an inner panel of gas-permeable liquid-impervious sheet material and an outer panel of flexible gas- and liquid-impervious sheet material; said outer panel being sealed to said one wall of said pouch along a continuous seal line spaced from and extending about said first flap vent to define a vent chamber between said outer panel and said one wall; wherein the improvement comprises said outer panel of said filter assembly being provided with a second flap vent in the form of a curvilinear slit defining at least one flap normally assuming a closed position coplanar with said outer panel but capable of flexing outwardly into said vent chamber to vent gases from said pouch; said flap of second flap vent being restrained against inward flexure by contact with said planar filter of said assembly; said first and second flap vents being out of register with each other.

7. The ostomy pouch of claim 6 in which each of said flap vents has the configuration of an S-shaped slit.

8. The ostomy pouch of claim 6 in which said one wall of said pouch has a dome-shaped portion aligned with said filter assembly, thereby spacing said one wall from said outer panel to form said vent chamber.

9. The ostomy pouch of claim 6 in which said planar filter includes a layer of porous odor-absorbing filter material and a cover layer of gas-permeable but water-repellent sheet material; said cover layer being disposed directly behind and immediately adjacent said outer panel of said filter assembly.

10. The ostomy pouch of claim 9 in which said cover layer and said outer panel are each formed of thermoplastic material and are heat sealed to each other along a second continuous seal line spaced from and extending about said second flap vent and inboard of said continuous seal line joining said outer panel to said one wall of said pouch.

\* \* \* \* \*